(12) United States Patent
Erdosy et al.

(10) Patent No.: US 6,896,793 B2
(45) Date of Patent: May 24, 2005

(54) LIQUID JUNCTION REFERENCE ELECTRODE AND METHODS OF USE THEREOF

(75) Inventors: Miklos Erdosy, North Chelmsford, MA (US); Vasile V. Cosofret, Acton, MA (US)

(73) Assignee: Instrumentation Laboratory Company, Lexington, MA (US)

(*) Notice: Subject to any disclaimer, the term of this patent is extended or adjusted under 35 U.S.C. 154(b) by 373 days.

(21) Appl. No.: 10/094,566

(22) Filed: Mar. 7, 2002

(65) Prior Publication Data

US 2003/0029722 A1 Feb. 13, 2003

Related U.S. Application Data

(60) Provisional application No. 60/274,097, filed on Mar. 7, 2001.

(51) Int. Cl.$^7$ ............................................. G01N 27/401
(52) U.S. Cl. ......................... 205/775; 204/409; 204/435
(58) Field of Search ................................. 204/409, 435; 205/775, 792, 789, 789.5, 787.5, 785.5; 73/1.02, 1.03

(56) References Cited

U.S. PATENT DOCUMENTS

| | | | |
|---|---|---|---|
| 3,658,478 A | | 4/1972 | Spergel et al. |
| 3,723,281 A | | 3/1973 | Wise |
| 3,915,829 A | * | 10/1975 | Krebs .......................... 204/435 |
| 4,179,349 A | * | 12/1979 | Park ............................. 204/404 |
| 4,214,968 A | | 7/1980 | Battaglia et al. |
| 4,271,474 A | | 6/1981 | Belanger et al. |
| 4,361,539 A | | 11/1982 | Weinberg et al. |
| 4,401,548 A | * | 8/1983 | Brezinski .................... 204/435 |
| 4,481,804 A | | 11/1984 | Eberhard et al. |
| 4,654,127 A | | 3/1987 | Baker et al. |
| 4,734,184 A | | 3/1988 | Burleigh et al. |
| 4,818,361 A | | 4/1989 | Burgess et al. |
| 4,818,365 A | | 4/1989 | Kinlen et al. |
| 4,871,439 A | | 10/1989 | Enzer et al. |
| 4,908,117 A | | 3/1990 | Kinlen et al. |

(Continued)

FOREIGN PATENT DOCUMENTS

| | | |
|---|---|---|
| EP | 0 094 677 | 11/1983 |
| EP | 0 125 136 A2 | 11/1984 |
| EP | 0 133 531 A1 | 2/1985 |
| EP | 0 133 531 B1 | 2/1985 |
| EP | 0 388 017 | 9/1990 |
| EP | 0 771 867 A2 | 5/1997 |
| EP | 0 772 041 A1 | 5/1997 |
| EP | 0 909 952 A3 | 4/1999 |
| WO | 94/19683 | 9/1994 |
| WO | 94/19684 | 9/1994 |

OTHER PUBLICATIONS

Emnéus et al., (1993) "Comparison Between Different Inorganic Supports for the Immobilization of Amyloglucosidase and α–amylase to Be Used in Enzyme Reactors in Flow–Injection Systems," *Analytica Chimica Acta*, 276:303–318.

Geise et al., (1991) "Electropolymerized Films to Prevent Interferences and Electrode Fouling in Biosensors," *Biosensors & Bioelectronics*, 6:151–160.

Ghindilis et al., (194) "Glucose Potentiometric Electrodes Based on Mediatorless Bioelectrocatalysis. A New Approach," *Biosensors & Bioelectronics*, 9:353–357.

(Continued)

Primary Examiner—Kaj K. Olsen
(74) Attorney, Agent, or Firm—Kirkpatrick & Lockhart Nicholson Graham LLP

(57) ABSTRACT

The invention relates to a durable and reliable miniature liquid junction reference electrode for use with at least one electrode (e.g., an electrochemical sensor cartridge) for measuring certain characteristics of a fluid sample such as blood or other body fluid.

36 Claims, 6 Drawing Sheets

U.S. PATENT DOCUMENTS

| | | | |
|---|---|---|---|
| 4,975,647 | A | 12/1990 | Downer et al. |
| 5,061,631 | A | 10/1991 | Calabrese et al. |
| 5,067,093 | A | 11/1991 | Przybylowicz et al. |
| 5,070,023 | A | 12/1991 | Calabrese |
| 5,103,179 | A | 4/1992 | Thomas et al. |
| 5,200,051 | A | 4/1993 | Cozzette et al. |
| 5,262,305 | A | 11/1993 | Heller et al. |
| 5,286,364 | A | 2/1994 | Yacynych et al. |
| 5,338,435 | A | 8/1994 | Betts et al. |
| 5,342,498 | A | 8/1994 | Graves et al. |
| 5,370,783 | A * | 12/1994 | Carlson et al. ............. 204/435 |
| 5,387,329 | A | 2/1995 | Foos et al. |
| 5,405,510 | A | 4/1995 | Betts et al. |
| 5,505,828 | A | 4/1996 | Wong et al. |
| 5,540,828 | A | 7/1996 | Yacynych |
| 5,653,862 | A | 8/1997 | Parris |
| 6,030,827 | A | 2/2000 | Davis et al. |
| 6,051,389 | A | 4/2000 | Ahl et al. |
| 6,123,820 | A | 9/2000 | Bergkuist et al. |
| 6,133,229 | A | 10/2000 | Gibson et al. |

OTHER PUBLICATIONS

Hart et al., (1999) "Estimation of Lactate in Meat Extracts by Screen–Printed Sensors," *Analytica Chimica Acta*, 386:7–12.

Lingene (1958) "Common Electrical Measurements," *Electroanalytical Chemistry* ($2^{nd}$ Ed.), Interscience Publishers, Inc., New York, 26–29.

Lingene (1958) "Controlled Potential Methodology," *Electroanalytical Chemistry* ($2^{nd}$ Ed.), Interscience Publishers, Inc., New York, 358–365.

Lipták et al. (eds.), (1982) "Ion Selective Electrodes," *Instrument Engineers' Handbook*, Chilton Book Co., Radnor, Pennsylvania, 655–703.

Mansouri et al., (1998) "Development of a Glucose Sensor and Its Inclusion in the GEM Blood Analyzer," *International Federation of Clinical Chemistry and Laboratory Medicine*, OmniPress, Madison, WI, USA, 368–379.

Patel et al., (2000) "Fabrication and Characterization of Disposable Type Lactate Oxidase Sensors for Dairy Products and Clinical Analysis," *Sensors and Actuators*, B 67:134–141.

"Reference Electrodes," http://www.epsilon–web.com/Ec/manual/Maintenance/reference.html (printed on Feb. 23, 2001).

Sasso et al., (1990) "Electropolymerized 1, 2–Diaminobenzene as a Means to Prevent Interferences and Fouling and to Stabilize Immobilized Enzyme in Electrochemical Biosensors," *Analytical Chemistry*, 62(11):1111–1117.

Waser (1961), "Quantitative Chemistry: A Laboratory Test," W.A. Benjamin, Inc., New York, 117–119, 207–208, 213–214, 223.

Yang et al., (1999) "Needle–type Lactate Biosensor," *Biosensors & Bioelectronics*, 14:203–210.

International Search Report for International Patent Application No. PCT/US02/07069, dated Feb. 4, 2003, 7 pages.

Suzuki et al., "Microfabricated Liquid Junction Ag/AgCl Reference Electrode and Its Application to a One–Chip Potentiometric Sensor", Anal. Chem., vol. 71, 1999, pp. 5069–5075.

* cited by examiner

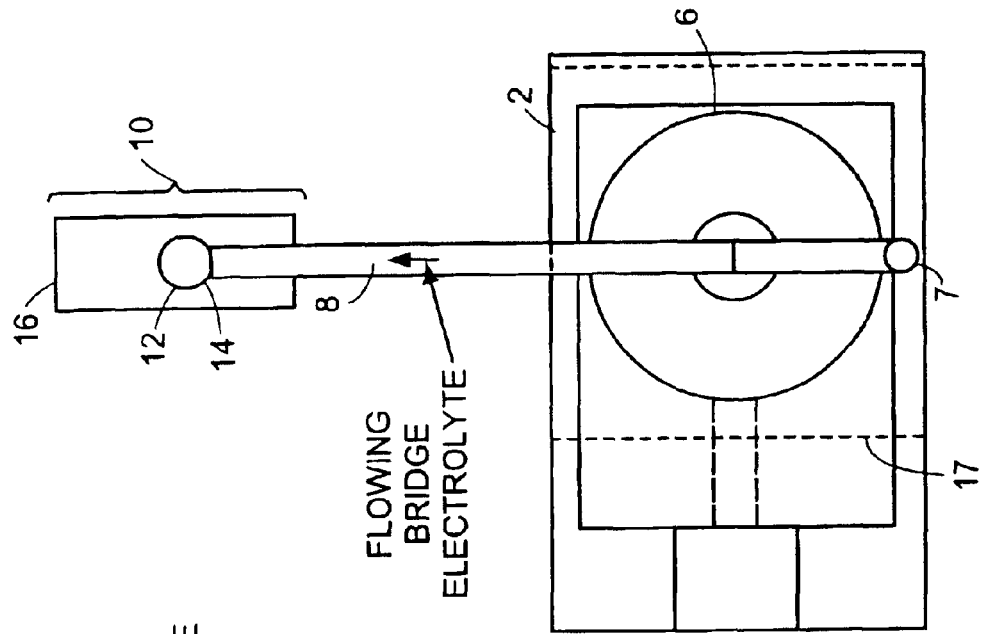
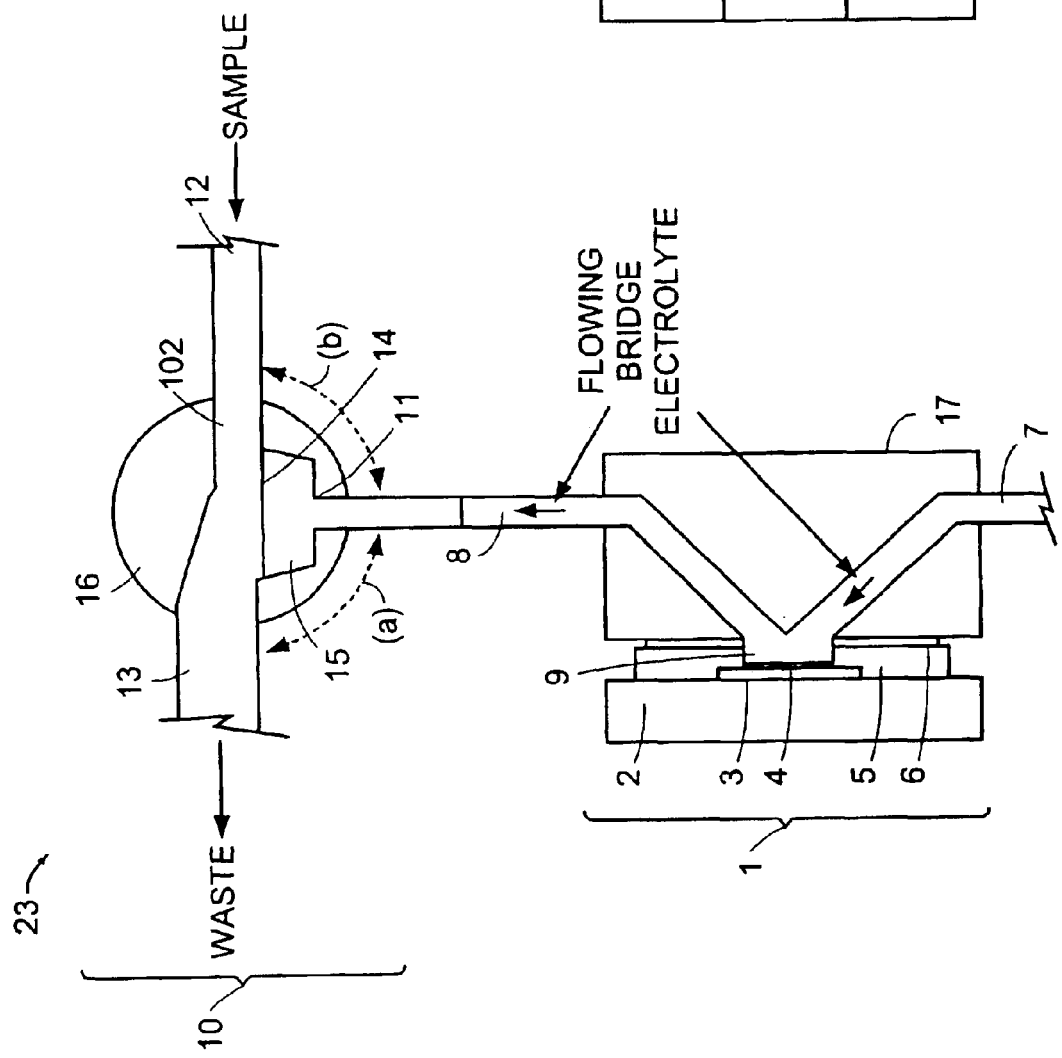
FIG. 1A
FIG. 1B

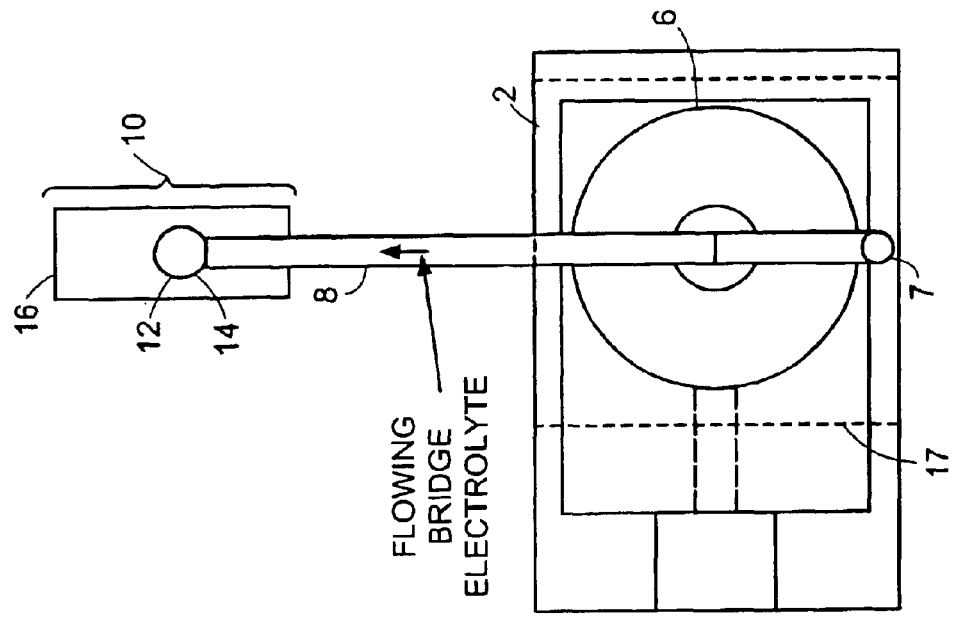
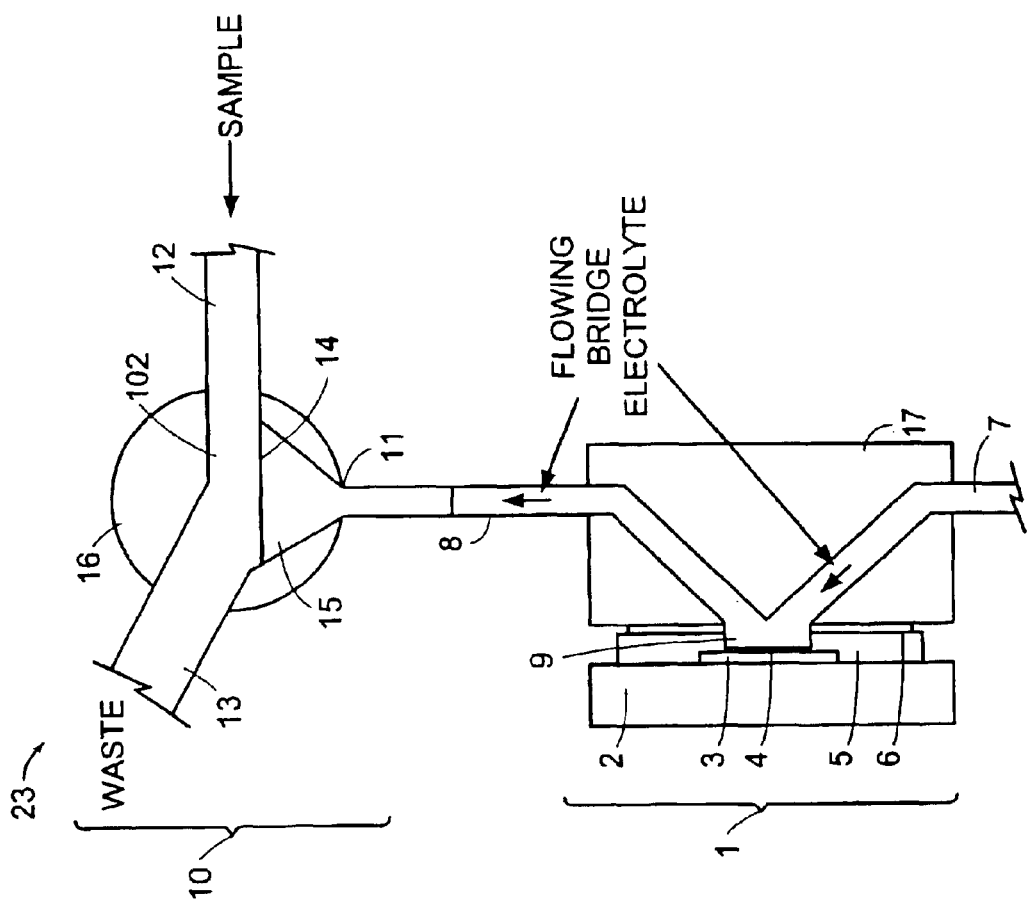
FIG. 2A
FIG. 2B

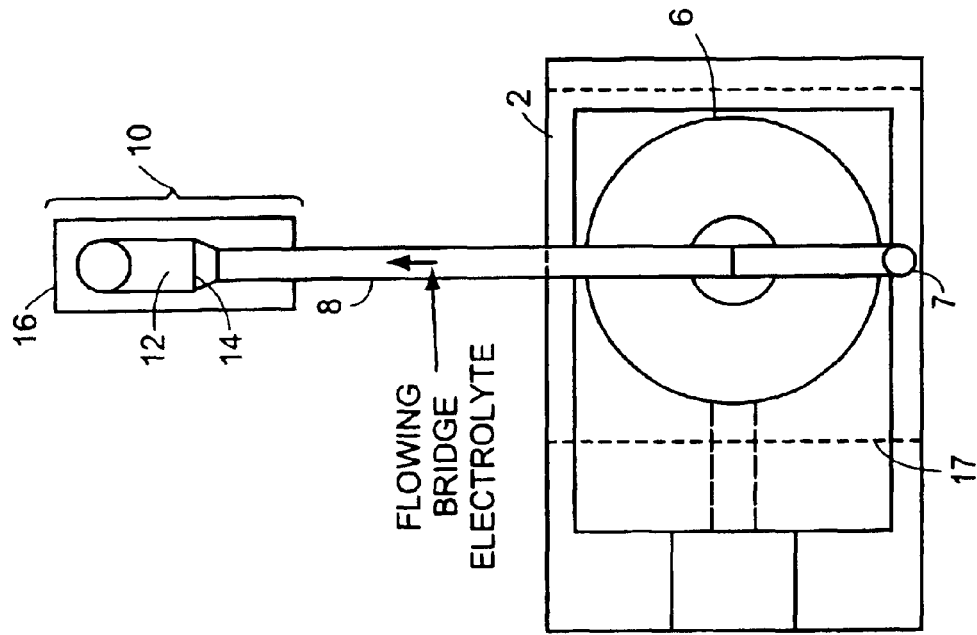
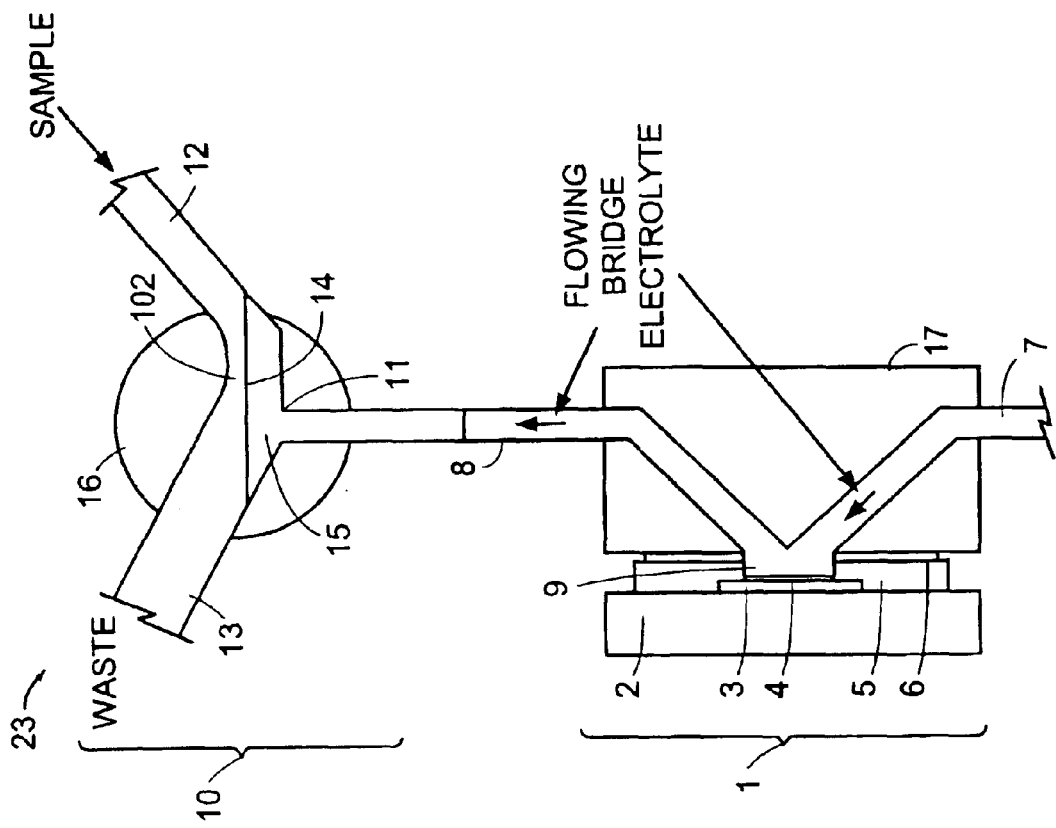
FIG. 3A
FIG. 3B

LIQUID JUNCTION REFERENCE ELECTRODE AND METHODS OF USE THEREOF

RELATED APPLICATIONS

This application claims priority to provisional patent application Ser. No. 60/274,097 filed in the U.S. Patent Office on Mar. 7, 2001, the entire contents of which is incorporated by reference herein.

FIELD OF THE INVENTION

The invention relates generally to liquid junction reference electrodes and methods of use thereof. In particular, the invention relates to miniature liquid junction reference electrodes for use with an electrochemical sensor cartridge for measuring certain characteristics of a fluid sample such as blood.

BACKGROUND OF THE INVENTION

It is often desirable in biomedical applications to analyze one or more physical properties and/or constituents of small volume samples of a patient's body fluid. For example, samples of a patient's whole blood are often analyzed and/or monitored to provide information regarding blood analytes such as pH, $pCO_2$, $pO_2$, $K^+$, $Na^+$, $Ca^{++}$, $Cl^-$, hematocrit and the like. Information derived from analytes in a blood sample is compared to normal physiological function and homeostasis profiles and may be used by a physician for diagnostic purposes, patient monitoring and/or for the control of life support systems, for example.

Systems which employ electrochemical electrodes for detecting constituents of a body fluid are well known in the art and are described, for example, in U.S. Pat. Nos. 3,658,478; 5,387,329; 5,338,435; 4,734,184; 4,361,539 and 5,200,051, the entire contents of which are hereby expressly incorporated by reference. Typically, systems which provide blood chemistry analysis are stand-alone machines or are adapted to be connected to an extracorporeal shunt or an ex vivo blood source, e.g., a heart/lung machine used to sustain a patient during surgery. Small test samples of flowing live ex vivo blood may be diverted off-line in real-time from either the venous or arterial flow lines of the heart/lung machine directly into a chamber and exposed to a bank of microelectrodes containing sensors which generate electrical signals proportional to, or indicative of, chemical characteristics of the real time flowing blood sample.

There have been efforts to miniaturize the sensors themselves and to fabricate them by techniques recently made available by developments in integrated circuit technology. In this regard, integrated circuit technology allows sensors to be fabricated in a planar form, whereby thin layers of materials are applied successively to a base dielectric substrate using thick-film and/or thin film techniques. The manufacture of planar sensors can be significantly automated to allow production in quantity and at lower cost. Planar sensors can be made smaller and configured more closely together, reducing the fluid sample volume requirements.

Though various miniature electrochemical sensors and Microsystems using such sensors have been developed, the unavailability of a durable, stable and reliable miniature reference electrode has restricted the use of miniature electrochemical sensors for industrial and biomedical applications. The stability of a reference electrode in potentiometry is very important for the reliability and accuracy of the measurements. A potential error of only 1 mV causes about a 0.02 pH error in pH measurements and 4% or 8% concentration error, respectively, for mono-and divalent ion measurements using ion-selective electrodes. Nevertheless, miniaturization has been largely limited to the development of working and indicator electrodes and, in many cases, commercial macro reference electrodes have been used in the absence of a reliable miniature reference electrode.

There have been several attempts to make miniature reference electrodes, as separate, independent units, as subcomponents in a multi-sensor structure, or integrated with various miniature ion-selective sensors. Typically, such systems use a thin film Ag/AgCl electrode. The thin film Ag/AgCl electrode is based on a very high exchange-current density reaction, i.e., at low current densities the electrode is not polarized and the potential at the electrode/ electrolyte interface is only a function of $Cl^-$ activity. However, several factors can limit the durability of the Ag/AgCl element. Conventional macro liquid-junction Ag/AgCl electrodes consist of a reservoir with a high activity of KCl, saturated with AgCl. Since AgCl shows some degree of solubility in high $Cl^-$ activities, a thin film of AgCl can ultimately dissolve depending on the temperature of the bridge electrolyte solution. In addition, the standard liquid junction miniature electrodes do not provide an adequate contact surface or liquid junction between a sample and the reference bridge electrolyte solution that completes the circuit for the reference electrode. A need therefore exists for an improved miniature reference electrode.

SUMMARY OF THE INVENTION

In one aspect, the invention provides a miniature liquid junction reference electrode which includes two components: a reference sensor and a connector. The reference sensor houses a durable thick-film Ag/AgCl element composed of a silver (Ag) layer deposited onto a support substrate and an AgCl layer formed onto the surface of the Ag layer by, e.g., electrochemical oxidation. In an embodiment, the reference sensor is connected to a bridge electrolyte inlet and a bridge electrolyte channel through which a bridge electrolyte solution may flow. The connector channel houses a connector channel including a sample inlet channel and a sample outflow channel through which a sample or calibration solution may flow. The connector also has a bridge electrolyte well and a bridge electrolyte port to which the bridge electrolyte channel is connected and through which the bridge electrolyte solution passes to contact a sample or a calibration solution.

The reference sensor may be composed of a number of layers that are deposited onto the support substrate, including: a silver (Ag) layer deposited on the support substrate, a silver chloride (AgCl) layer formed on the Ag layer, a glaze layer deposited on part of the AgCl layer, and a polymeric gasket placed on the glaze layer. The layers may be deposited by any means but are preferably deposited by screen printing or vapor deposition.

The support substrate is made of, for example, a polymeric material and/or a ceramic material. The polymeric material may, for example, be a flexible or hard polyvinyl chloride, polyethylene, polycarbonate, polyacrylate and/or polyimide. The ceramic material may be, for example, aluminum oxide and/or silicium dioxide.

The Ag layer may be at least about 1 $\mu$m about 1 $\mu$m to about 15 $\mu$m or is preferably about 15 $\mu$m thick.

The AgCl layer may be formed, for example, on the Ag layer by electrodeposition. In an embodiment, the AgCl layer is formed on the Ag layer by treatment of the Ag layer with a chloride electrolyte solution having a concentration of between 0.01 and 1.0 M with a current density of between about 0.0005 and about 0.5 mA/mm² for about 30 seconds to about 20 minutes. The chloride electrolyte solution may be, for example, NaCl, KCl, or $CaCl_2$, and may have a pH range between about pH 1 and about pH 7, between about pH 1 and about pH 5 or between about pH 1 and about pH 2.

The glaze layer may be composed of, for example, alumina and/or silica and is between 10 µm and 500 µm and is at least about 10 µm thick.

The polymeric gasket layer may be made of, for example, polyurethane, silicone rubber, PVC, natural and/or synthetic rubber (e.g., viton®), or any other flexible material that does not react with or dissolve in the bridge electrolyte solution. The polymeric gasket layer is at least about 50 µm thick. In a preferred embodiment, the polymeric gasket layer is between about 50 µm and about 700 µm thick. The bridge electrolyte channel which connects to and passes over the reference sensor is preferably, but not limited to, about 0.5 mm in diameter.

The connector channel is made of, for example, a polymeric or metallic material that should not react with, or dissolve in, the bridge electrolyte solution. Suitable metallic materials include stainless steel, aluminum and/or platinum. Suitable polymeric materials include acrylic, plexiglas®, lexan®, polycarbonate, and/or PVC. The bridge electrolyte port of the connector channel is preferably close to the reference sensor, located at a distance range from between about 2 mm to about 10 mm, between about 2 mm to about 15 mm, or between about 2 mm to about 30 mm from the reference electrode. The sample inlet channel of the connector is preferably, but not limited to, about 1 mm in diameter. The sample outflow channel is preferably, but not limited to, about 2 mm in diameter. The sample outflow channel and the sample inlet channel of the connector channel are composed of one or more tubes that are connected together and have a common lumen. For example, the sample inlet channel and sample outflow channel may be a flexible tube, preferably, but not limited to, about 1 mm to about 30 mm in diameter. In an embodiment, each of the sample outflow channel and sample inlet channel are oriented at a tilt angle of about 90° to about 180° relative to the longitudinal axis of the bridge electrolyte channel. This manner of tilting or bending the sample channel may create a bridge electrolyte well above the bridge electrolyte port.

The bridge electrolyte port defines a hole which connects the bridge electrolyte channel to the connector channel. The connector channel proximate to the bridge electrolyte port is shaped to form a bridge electrolyte well capable of holding a volume of bridge electrolyte solution. The bridge electrolyte well may be, e.g., flat bottomed, round bottomed or cone shaped. In a preferred embodiment, the connector channel or bridge electrolyte well is shaped so as to hold a volume of bridge electrolyte solution. The liquid junction formed in the bridge electrolyte well between a sample and the bridge electrolyte solution has a surface area in the range of about 1 mm² to about 10 mm² when the reference electrode is in use. When a sample is passed (e.g., pumped) over the bridge electrolyte well which contains the bridge electrolyte solution, a sample/bridge electrolyte solution liquid junction (i.e., interface) forms. In an embodiment, the surface area of the liquid junction is at least about 0.05 mm² to about 10 mm².

The bridge electrolyte solution used in the reference electrode is preferably KCl saturated with AgCl, with a chloride ion solution of about 0.1 M to about 0.5 M at the temperature the solution is stored and used.

In another aspect the invention relates to methods for using a liquid junction reference electrode, involving using the reference electrode for measuring one or more electrolytes or enzymes in a sample. In an embodiment, the reference electrode is connected to an electrode sensor cartridge for measuring one or more analytes. The methods of using the reference electrode involves the following steps: providing a calibration solution or sample to a sample inlet channel; providing a bridge electrolyte solution to the bridge electrolyte inlet; providing a force to the sample or calibration solution and a force to the bridge electrolyte solution so that each of them flows toward the bridge electrolyte port; forming a contact interface or liquid junction in the bridge electrolyte well between the sample and the bridge electrolyte solution; and taking a measurement after a period of time (e.g., when the readout value settles). The force used to move the sample through the connector channel and the bridge electrolyte solution through the bridge electrolyte channel may be caused by positive or negative pressure by one or more peristaltic pumps.

BRIEF DESCRIPTION OF THE DRAWINGS

The foregoing and other objects, features and advantages of the present invention disclosed herein, as well as the invention itself, will be more fully understood from the following description of preferred embodiments and claims, when read together with the accompanying drawings, in which:

FIG. 1A illustrates a schematic cross sectional view of an embodiment of a reference electrode in which the bridge electrolyte well is a flat bottom cup.

FIG. 1B illustrates a side view of the reference electrode illustrated in FIG. 1A.

FIG. 2A illustrates a schematic cross-sectional view of an embodiment of a reference electrode in which the bridge electrolyte well is cone shaped.

FIG. 2B illustrates a side view of the reference electrode illustrated in FIG. 2A.

FIG. 3A illustrates a schematic cross-sectional view of an embodiment of a reference electrode in which the bridge electrolyte well is formed by bending the sample inlet channel and/or the sample outflow channel to a tilt angle of greater than about 90°.

FIG. 3B illustrates a side view of the reference electrode illustrated in FIG. 3A.

In the drawings, like reference characters generally refer to the same parts throughout the different views. The drawings are not necessarily to scale, emphasis instead generally being placed upon illustrating the principles of the invention.

DETAILED DESCRIPTION OF THE INVENTION

Figure 1C:
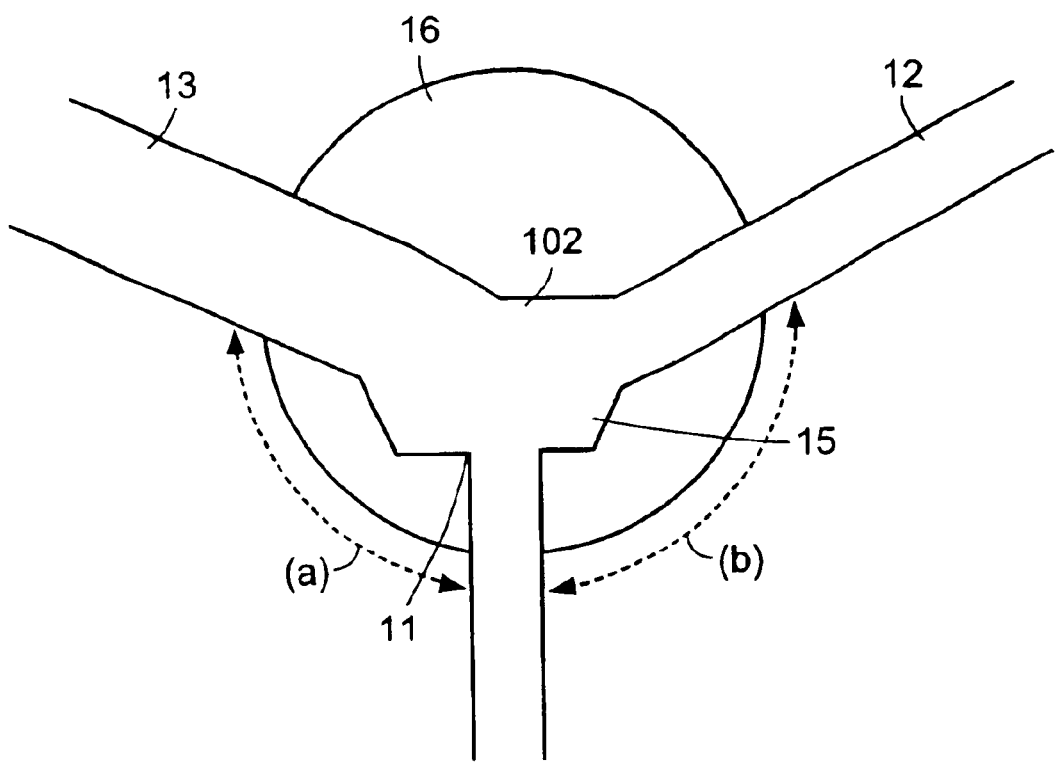
FIG. 1C illustrates an embodiment of the bridge electrolyte well of the connector channel according to the invention.

The present invention provides a reference electrode for use with a miniature electrochemical sensor cartridge for measuring characteristics of fluid samples such as body fluids, including, but not limited to, blood. The reference electrode is useful as a durable reference source for measuring the unbound concentration or activity of blood gases (such as, e.g., oxygen and carbon dioxide), ions (such as, e.g., sodium, chloride, potassium, magnesium, lithium, ammonium and calcium), blood pH and hematocrit. Alternative embodiments of the invention may be adapted to measure factors such as glucose, lactate or other enzymes or blood solutes.

Definitions

In order to more clearly and concisely point out and describe the subject matter of the invention, the following definitions are provided for certain terms used in the following description and claims.

As used herein, the term "electrode" refers to a component of an electrochemical device that makes the interface between an external electrical conductor and the internal ionic medium. The internal ionic medium is typically an aqueous solution with dissolved salts. Electrodes are generally of three types, working or indicator electrodes, reference electrodes, and counter electrodes. A working or indicator electrode measures a specific chemical species, such as an ion. When electrical potentials are measured by a working electrode, the method is termed potentiometry. All ion-selective electrodes operate by potentiometry. When current is measured by a working electrode, the method is termed amperometry. Oxygen measurement, for example, is carried out by amperometry. A counter electrode acts as a sink for current path.

A "reference electrode" according to the invention refers to the combination of a reference sensor, through which bridge electrolyte solution passes and a connector, through which a sample or calibration fluid flows. The reference sensor generally serves as an electrical reference point in an electrochemical device against which electrical potentials are measured and controlled.

As used herein, the term "sensor" or "electrochemical sensor" is a device that responds to variations in the concentration of a given chemical species in a sample, such as a body fluid sample. For ion-selective measurements, the sensor is normally used with a reference electrode containing a reference sensor. A reference sensor is a sensor that is used in a reference electrode. In one embodiment, the reference sensor includes silver-silver chloride-potassium chloride. Other types of reference sensors are mercury-mercurous chloride-potassium chloride or silver-silver nitrate.

As used herein, the term "liquid junction" refers to the interface between the bridge electrolyte solution and a sample or calibrating solution.

As used herein, the term "sample" refers to any fluid or solution which may be tested using the reference electrode, including, for example, an aqueous solution, such as a reference or calibrating solution, or a body fluid, such as blood, plasma, synovial fluid, and urine.

As used herein, the term "calibration" refers to the process by which the response characteristics of a sensor to a specific analyte are determined quantitatively. To calibrate a sensor, the sensor is exposed to at least two reagent samples or calibrating solutions, each reagent sample having a different, known concentration of an analyte. The responses (i.e., signals) measured by the sensor, relative to the concentrations of the analyte in the two different reagent samples, serve as reference points for measurements of the analyte in samples having unknown concentrations of the analyte.

The "support substrate" as used herein refers to the substrate of a sensor upon which the various layers (such as, e.g., Ag, AgCl, glaze, gasket etc.) of the sensor are applied, formed, or deposited.

The "connector" as used herein refers to the component of the reference electrode including a connector channel which includes a sample inlet channel and a sample outflow channel, the bridge electrolyte port to which the bridge electrolyte channel is joined and the connector housing.

The "tilt angle" of the sample inlet channel refers to the angle between the sample inlet channel and the longitudinal axis of the bridge electrolyte channel. The "tilt angle" of the sample outflow channel refers to the angle between the sample outflow channel and the longitudinal axis of the bridge electrolyte channel.

A "bridge electrolyte well" is the portion of the connector shaped to retain a volume of the bridge electrolyte solution.

Assembly of the Reference Electrode: The Reference Sensor

In one embodiment according to the invention, the reference electrode 23 illustrated in FIG. 1A and FIG. 1B includes a reference sensor 1 and a connector 10. Referring to FIG. 1A, the reference sensor 1 is the portion of the reference electrode 23 that is made up of a support substrate 2, an Ag layer 3, AgCl layer 4, a glaze layer 5 and a gasket layer 6. A bridge electrolyte inlet 7 is a conduit that connects to the bridge electrolyte channel 8, through which bridge electrolyte solution may flow. A bridge electrolyte channel 8 is a channel that connects the bridge electrolyte inlet 7 to the bridge electrolyte port 11. To operate the reference electrode 23, a bridge electrolyte solution is pumped through the bridge electrolyte inlet 7, over the Ag/AgCl layers 3, 4, through the bridge electrolyte channel 8, through the bridge electrolyte port 11 and into the bridge electrolyte well 15 where the bridge electrolyte solution contacts, e.g., a calibration solution or sample in the bridge electrolyte well 15, creating a fluid junction or interface 14 between the bridge electrolyte solution and the sample.

In one embodiment, the support substrate 2 of the reference electrode 23 is made of a polymeric material or a ceramic material or a combination thereof. The polymeric material may be, for example, polyvinyl chloride, polyethylene, polycarbonate, polyacrylate, or polyimide or a combination thereof. The ceramic material may be, for example, aluminum oxide or silicium dioxide or a combination thereof.

Referring still to FIGS. 1A and 1B, an Ag layer 3 is deposited onto the support substrate 2 by, e.g., screen printing or vapor deposition, according to art known methods. For screen printing, the Ag particles may be combined with ceramic binding material and then screen printed, followed by firing at high temperature (e.g., 700–800° C.), for example. For vapor deposition, Ag metal may be evaporated and condensed onto the support substrate 2 under high vacuum, for example.

In one embodiment according to the invention, referring still to FIGS. 1A and 1B, the AgCl layer 4 of the reference electrode 23 is formed by electrodeposition of the Ag layer 3 with a chloride electrolyte solution having a concentration of between about 0.01 M and 1.0 M and a pH of about pH 1 to about pH 7 at a current density of 0.005 to 0.5 mA/mm$^2$ for 30 seconds to 20 minutes. In a preferred embodiment, electrodeposition is performed with a chloride electrolyte solution having a current density of the chloride electrolyte of about 0.05 mA/mm$^2$ for 6 minutes.

With continued reference to FIGS. 1A and 1B, the glaze layer 5 of the reference electrode 23 may be composed of alumina and/or silica and is at least about 10 μm thick. The glaze layer 5 is sized and shaped to cover any portion of the Ag layer 3 that is not covered with an AgCl layer 4 and provides insulation of the Ag layer 3 which is not oxidized to form an AgCl layer 4 (e.g., around the edges of the Ag layer 4). Referring still to FIGS. 1A and 1B, the glaze layer 5 also forms the walls of a well 9 around the AgCl layer 4 as high as the thickness of the glaze layer 5. The insulating glaze layer 5 is then covered with the gasket layer 6.

The gasket layer 6 is preferably made of polyurethane, silicone rubber, polyvinylchloride (PVC), viton®, natural or synthetic rubber, and/or any other flexible material that does not react with, or dissolve in, the bridge electrolyte solution. The gasket layer 6 is at least about 50 μm thick. In a preferred embodiment, the gasket layer 6 is between about 50 μm and about 700 μm thick. The gasket layer 6 is shaped to cover the glaze layer 5.

The bridge electrolyte inlet 7 provides a conduit for bridge electrolyte solution which flows through the bridge electrolyte channel 8, passing over the reference sensor 1. In one embodiment, referring to FIGS. 1A and 1B, the bridge electrolyte inlet 7 and bridge electrolyte channel 8 are housed in an acrylic block 17.

The Connector

Referring to FIG. 1A, in general, the connector 10 has a connector channel 102 including a sample inlet channel 12 and a sample outflow channel 13 which leads to a waste collection container (not shown), a bridge electrolyte port 11, a bridge electrolyte well 15 and a connector housing 16. The bridge electrolyte channel 8 is connected to the connector 10 via the bridge electrolyte port 11. The sample inlet channel 12 is a conduit for the flow of a fluid sample such as blood or a calibration solution over the bridge electrolyte well 15, to the sample outflow channel 13 and then to a waste container.

In one embodiment of the invention, the connector 10 is formed in the shape of a T as illustrated in FIG. 1A. In this embodiment, the sample inlet channel 12 and the sample outflow channel 13 are essentially perpendicular (i.e., about 90°) to the longitudinal axis of the bridge electrolyte channel 8. In this orientation, the tilt angle (b) of the sample inlet channel 12 relative to bridge electrolyte channel 8, and the tilt angle (a) of the sample outflow channel 13 relative to bridge electrolyte channel 8, are about 90°. The 90° tilt angle (a), (b) shown in FIG. 1A is merely illustrative and any angle between about 90° and about 180° is contemplated by the invention. For example, as illustrated in FIG. 1C, the tilt angle (a) of the sample outflow channel 13 may be 150° and tilt angle (b) of the sample inlet channel 12 may be 120°.

Several embodiments of the bridge electrolyte well 15 are show in FIGS. 1A, 2A and 3A. Referring to FIG. 1A, in one embodiment the bridge electrolyte well 15 can be substantially flat-bottomed. Referring to FIG. 2A, in another embodiment the bridge electrolyte well 15 can be substantially cone-shaped. Referring to FIG. 3A, in yet other embodiment the bridge electrolyte well 15 is formed at a bend in the connector channel 102 when the tilt angle (a) of the sample inlet channel 12 and/or the tilt angle (b) of the sample outflow channel 13 is greater than about 90° relative to the longitudinal axis of the bridge electrolyte channel 8. Any upward bend of one or both of the sample inlet channel 12 or sample outflow channel 13 which creates a bridge electrolyte well 15 is contemplated. A bridge electrolyte well 15 is created in the connector channel 102 just above the bridge electrolyte port 11 which can hold a volume of bridge electrolyte solution. When a fluid sample or calibrating solution interfaces with the bridge electrolyte solution in the bridge electrolyte well 15, a liquid junction 14 is created between the sample or calibrating solution and the bridge electrolyte solution. In one embodiment, the bridge electrolyte well 15 retains 10 μl to 500 μl of bridge electrolyte solution. In a particular embodiment of the invention, the liquid junction 14 preferably has a surface area in the range of about 0.5 mm² to about 10 mm².

The connector 10 is made of a material that does not react with, or dissolve in, the bridge electrolyte solution used in the reference electrode 23. In one embodiment, the connector 10 is metallic and is made of, for example, stainless steel, aluminum and/or platinum. In another embodiment, the connector 10 is made of a polymeric material, for example, acrylic, plexiglas®, lexan®, polycarbonate, and/or PVC.

Operation of the Reference Electrode

In another aspect, the invention is a method for using a reference electrode 23 in a sensor system for measuring an analyte in a fluid sample. Referring to FIG. 1A, the bridge electrolyte solution is introduced into the bridge electrolyte inlet 7, and passes over and comes into contact with the reference sensor Ag/AgCl layers 3, 4, the fluid is pumped through the bridge electrolyte channel 8, through the bridge electrolyte port 11 into the bridge electrolyte well 15. When a fluid sample is introduced into the sample inlet channel 12, e.g., by positive flow by peristaltic pump, it comes into contact with the bridge electrolyte solution in the bridge electrolyte well 15, forming the liquid junction 14. The contact of sample with the bridge electrolyte solution completes the circuit of the reference electrode 23.

The Sensor Cartridge

Figure 4:
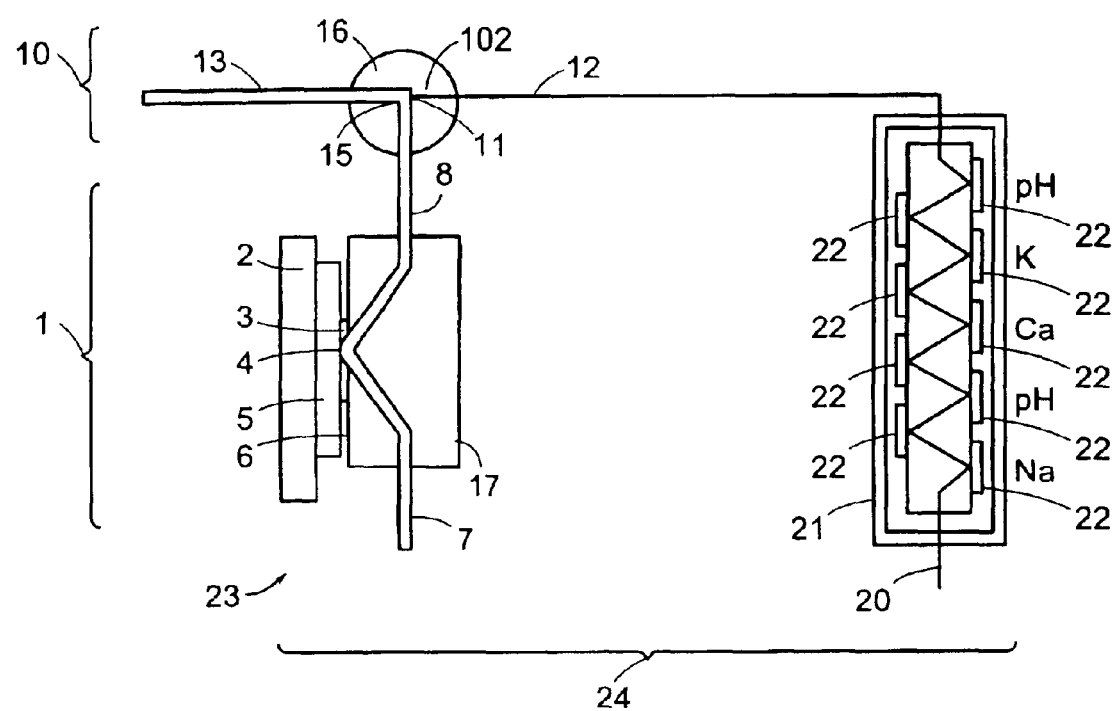
FIG. 4 is a schematic view of the reference electrode being used with an electrochemical sensor cartridge.

Referring to FIG. 4, in a particular embodiment of the invention, the reference electrode 23 is used in conjunction with at least one sensor 22, or a sensor cartridge 21 incorporating a plurality of sensors 22, connected by a cartridge inlet channel 20 adapted to make electrical measurements on a sample introduced to the sensor cartridge 21. Preferred sensor cartridges 21 are set forth in detail in U.S. Pat. Nos. 4,734,184 and 6,123,820, which are incorporated by reference herein. The sensor cartridge 21 may contain, for example, electrochemical sensors (i.e., electrodes) 22 for measuring, e.g., pH, $pCO_2$, $pO_2$, $Na^+$, $Ca^{++}$, and hematocrit, together with the reference electrode 23. Alternatively, the sensor cartridge 21 may contain enzyme sensors 22. Temperature control may be achieved by employing a suitable heating or cooling element e.g., a Peltier-effect device and thermistor to maintain the sensor cartridge 21 at a desired temperature.

Sensor Cartridge—Reference Electrode Assembly

Referring to FIG. 4, the sensor cartridge 21 and the reference electrode 23 and the various channels leading in and out of the sensor cartridge 21 and reference electrode 23 (e.g., bridge electrolyte inlet 7, bridge electrolyte channel 8, sample inlet channel 12, sample outflow channel 13, cartridge inlet channel 20) are assembled into a sensor cartridge-reference electrode assembly 24 ("assembly 24").

Figure 5:
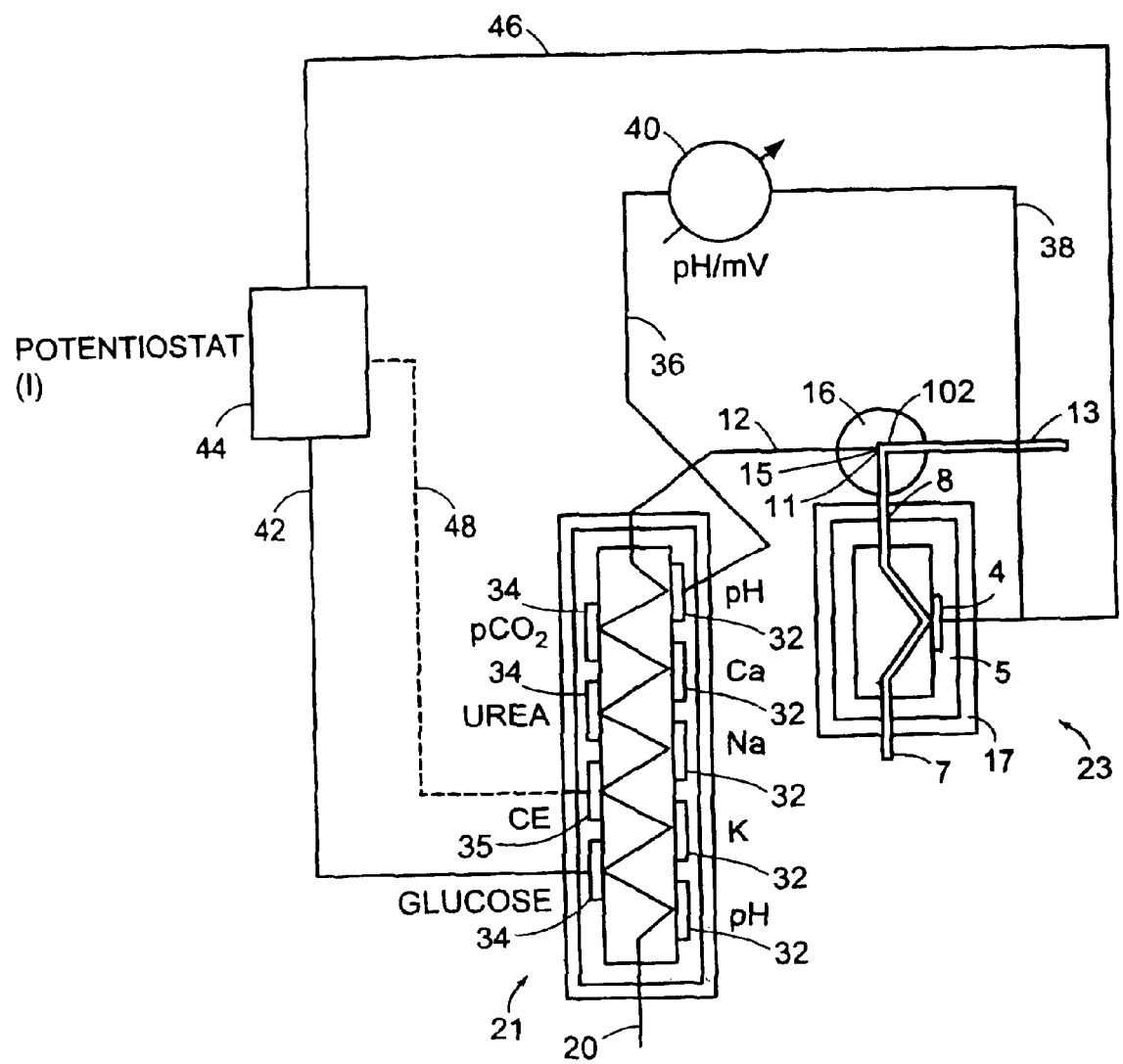
FIG. 5 is a schematic view of the reference electrode connected to a sensor cartridge via a sample inlet channel, a pH/mV meter and a potentiostat, with optional connection of the potentiostat to a platinum or gold electrode.

FIG. 5 illustrates an embodiment of the invention in which a reference electrode 23 is connected to a sensor cartridge 21 via a sample inlet channel 12, a pH/mV meter 40 and a potentiostat 44, with optional connection of the potentiostat 44 to a platinum or gold electrode 35, for use in obtaining potentiometric and amperometric measurements. For potentiometric sensors (e.g., pH, $Na^+$, $K^+$, etc.), one lead of a pH/mV meter 40, i.e., a first pH/mV meter input lead 36, is connected to each potentiometric sensor 32, and the other lead of a pH/mV meter 40, i.e., a second pH/mV meter input lead 38, is connected to the reference electrode 23. FIG. 5 provides an exemplary illustration of the first pH/mV meter input lead 36 of the pH/mV meter 40 connected to a pH sensor 32 and the second pH/mV meter input lead 38 of the pH/mV meter 40 connected to the reference electrode 23;

however, additional pH/mV meter input leads 36, 38 may connect the pH/mV meter 40 with additional potentiometric sensors (e.g., for $Ca^{++}$, $Na^+$, and $K^+$) 32 and the reference electrode 23. The pH/mV meter 40 measures the potential difference between the potentiometric sensors 32 and the reference electrode 23. This potential difference is proportional to the concentration of the analyte in the sample or calibrating solution.

Referring still to FIG. 5, for amperometric sensors (i.e., working electrodes) 34 (e.g., $pO_2$, glucose, lactate, urea, $pCO_2$, etc.) in a two electrode type cell arrangement, one lead of the so-called potentiostat 44, i.e., the working electrode connection 42, is connected to each amperometric sensor 34, and the other lead of the potentiostat 44, i.e., the reference electrode connection 46, is connected to the reference electrode 23. FIG. 5 provides an exemplary illustration of the working electrode connection 42 of the potentiostat 44 connected to a glucose sensor 34 and the reference electrode connection 46 of the potentiostat 44 connected to the reference electrode 23; however, additional potentiostat leads 42, 46 may connect the potentiostat 44 with additional amperometric sensors 34 and the reference electrode 23. In the case of a three-electrode type amperometric cell arrangement, a third lead of the potentiostat 44, i.e., the counter electrode (CE) connection 48, is connected to a platinum or gold electrode 35 (as illustrated with a hatched line in FIG. 5), which is in direct contact with the sample or calibrating solution. The potentiostat 44 applies a predetermined potential between the sensors 34 and the reference electrode 23. The current, flowing through the sensor 34 and measured by the potentiostat 44 is proportional to the concentration of the analyte in the sample or calibrating solution.

The details of sensors such as ion-selective electrodes and their manufacture for a sensor cartridge as well as peristaltic pump systems employed are described in U.S. Pat. Nos. 4,214,968, 4,734,184, 6,123,820 and the operation of microelectrodes is described in detail in U.S. Ser. No. 60/170,136, the contents of all of which are incorporated by reference herein.

A sensor cartridge-reference electrode assembly 24 needs to be calibrated prior to determining the concentration of an analyte in a sample. The sensors 22 of the sensor cartridge 21 may be calibrated with at least one aqueous solution having a known value for the parameters to be measured by the assembly 24. Two calibrating solutions having different known values for a particular analyte allows the system to be calibrated on a 2-point basis. Referring to FIG. 4, for calibration of the assembly 24, a first peristaltic pump causes the first calibrating solution to move (e.g., to be pulled) into the cartridge inlet channel 20 and to pass through the sensor cartridge 21 over one or more sensors 22. A second peristaltic pump causes bridge electrolyte solution to move (e.g., to be pushed) into the bridge electrolyte inlet 7, over the reference sensor Ag/AgCl layers 3, 4 and into the bridge electrolyte channel 8. The bridge electrolyte solution then moves through the bridge electrolyte channel 8 toward the connector 10, where it forms a liquid junction 14 with the first calibrating solution. In a particular embodiment of the invention, the liquid junction 14 is formed between about 10 µl to about 500 µl of bridge electrolyte solution in the bridge electrolyte well 15 and about 10 µl to about 300 µl of sample or a first calibration solution in the connector channel 102. After the liquid junction 14 has formed, the first peristaltic pump and the second peristaltic pump are stopped. After about 20 to about 90 seconds, while the transient signals are stabilized for the sensors 22, a measurement (e.g., a potential value) is obtained. The same procedure may be repeated using a second calibrating solution. In one embodiment, a calibrating solution may be used to provide a baseline reading for the assembly 24. A sample such as a blood sample is then measured using a similar cycle. In one embodiment, after a sample is measured, a rinsing solution (e.g., a calibration solution) may be used to clean the sensor cartridge 21, cartridge inlet channel 20, sample inlet channel 12, sample outflow channel 13, bridge electrolyte well 15 and/or liquid junction 14. After washing, the first calibrating solution is loaded into the sample inlet channel 20 of the sensor cartridge 21, the bridge electrolyte solution is refreshed by pumping fresh bridge electrolyte solution through the bridge electrolyte inlet 7 and bridge electrolyte channel 8 into the bridge electrolyte well 15. The assembly 24 is then ready for the next sample.

In one embodiment, during operation of the pump, the cartridge—reference electrode assembly 24 receives a constant pulsating flow of the bridge electrolyte solution via the bridge electrolyte inlet 7 and pulsating flows of either the blood sample or one of the two calibrating solutions via the cartridge inlet channel 20. In an embodiment, during the time when the sensor cartridge—reference electrode assembly 24 is ready for the next sample or calibration, one of the calibration solutions (preferably the second calibrating solution) is in front of the sensors so that a constant baseline calibration reading can be maintained over time and between samples.

A microprocessor may control the activity of the pump to cause sequences of fluid samples, calibrating solutions and rinsing solutions (e.g., the second calibration solution) to be passed through the assembly 24 as is well known in the art. When the calibrating solutions are passed through the assembly 24, the sensors 22 forming part of the assembly 24 make measurements of the parameters of the sample and the microprocessor stores these electrical values. Based upon measurements made during the passage of the calibration solutions through the sensor cartridge 24, and the known values of the measured parameters contained within the calibrating solutions, the microprocessor may create a calibration curve for each of the measured parameters so that when a sample is passed through the assembly 24 the measurements made by the sensors 22 can be used to derive accurate measurements of the parameters of interest. These measurements are stored and displayed by the microprocessor. The microprocessor is suitably programmed to perform measurement, calculation, storage, and control functions.

Blood Samples

Blood samples may be obtained by phlebotomy or are derived on a periodic basis from an extracorporeal blood flow circuit connected to a patient during, for example, open heart surgery. Blood samples may be introduced into the cartridge inlet channel 20 through other automatic means, or manually (e.g., as by syringe). Blood samples may also be introduced as discrete samples.

Calibrating Solutions

In an embodiment, the sensor cartridge-reference electrode assembly 24 may be calibrated with two calibrating solutions, e.g., calibrating solution A and calibrating solution B. A preferred composition of calibrating solution A, prepared at 37° C. and at atmospheric pressure tonometered with 8% $CO_2$—92% $N_2$ gas, is as follows:

| Compound | Amount/1 Liter |
| --- | --- |
| Deionized water | Filled up to 1 liter |
| MOPS (3-[N-morpholinopropanesulfonic acid) Buffer | 16.5 g |
| Sodium MOPS Buffer | 8.2 g |
| Sodium Sulfite | 5.0 g |
| Potassium Chloride | 0.17 g |
| Calcium Chloride | 0.068 g |
| Sodium Chloride | 2.76 g |
| Sodium Bicarbonate | 1.26 g |
| Proclin | 1.015 g |
| HCl | 0.15 g |
| Brij (from a 25% solution as surfactant) | 0.256 g |

This composition is effectively a blood facsimile and has the following parameters to be measured by the assembly 24.

| pH | $pCO_2$ (mmHg) | $O_2$ (mmHg) | Na (mmol/L) | K (mmol/L) | Ca (mmol/L) |
| --- | --- | --- | --- | --- | --- |
| 6.908–6.932 | 60.5–64.5 | 0 | 153.5–156.5 | 1.81–2.11 | 0.18–0.22 |

A preferred composition of calibration solution B, prepared at 37° C. and at 700 mmHg absolute pressure tonometered with 21% $O_2$—4% $CO_2$—75% $N_2$ gas, is as follows:

| Compound | Amount/1 Liter |
| --- | --- |
| Deionized water | Filled up to 1 liter |
| MOPS (3[N-morpholinopropanesulfonic acid) Buffer | 6 g |
| Sodium MOPS Buffer | 18.75 g |
| Sodium sulfate | 3.75 g |
| Magnesium Acetate | 1.07 g |
| Potassium Chloride | 0.527 g |
| Calcium Chloride | 0.535 g |
| Sodium Chloride | 0.13 g |
| Sodium bicarbonate | 1.932 g |
| Proclin | 1.023 g |
| HCl | 0.313 g |
| Brij (from a 25% solution as surfactant) | 0.256 g |

This composition is effectively a blood facsimile and has the following parameters to be measured by the assembly 24.

| pH | $pCO_2$ (mmHg) | $O_2$ (mmHg) | Na (mmol/L) | K (mmol/L) | Ca (mmol/L) |
| --- | --- | --- | --- | --- | --- |
| 7.385–7.415 | 33.0–37.0 | 190–210 | 133–137 | 5.87–6.27 | 1.90–2.04 |

The compositions of the two calibrating solutions are chosen so that for each of the characteristics measured by the system, a pair of values are obtained that are spaced over the range of permissible values that are measured by the assembly 24, providing a balanced 2-point calibration for the assembly 24.

The calibration compositions are prepared by premixing all of the components, with the exception of the calcium dihydrate salt; tonometering the solution with oxygen and $CO_2$ mixed with nitrogen to produce the desired level of pH for the solution; adding the calcium dihydrate salt; and finally retonometering the solution to adjust for any variation in the gas levels which occurred during addition of the calcium dihydrate salt.

The compositions of calibrating solutions A and B are for illustrative purposes; it is contemplated that any desired calibrating solution may be used with the reference electrode 1.

Bridge Electrolyte Solution

The bridge electrolyte solution employed in the reference electrode 23, for example, as illustrated in FIG. 1A, provides a liquid junction 14 with a sample or a calibration solution and thereby isolates the reference electrode 23 from the varying electrochemical potentials of the calibrating solution or the blood to establish an environment in the reference electrode 23 that is independent of the ionic activity of the sample or calibrating solution. The bridge electrolyte solution is essentially a chloride solution (e.g., KCl) that is hypertonic relative to the sample or calibrating solutions.

Since the bridge electrolyte solution joins the sample inlet channel 12 downstream from the sensors 22, after the gas/electrolyte measurements have been made, it does not affect those measurements in any way. The bridge electrolyte solution is under pumping force must flow upward against gravity toward the bridge electrolyte well 15. Thus, when the pump stops, the bridge electrolyte solution remains stationary in the bridge electrolyte well 15 of the connector 10 and tends not to diffuse significantly into the calibrating solution or sample in the sample inlet channel 12, preventing unwanted reverse passage or mixing of the sample or calibrating solution into the reference sensor 1. It is important that the bridge electrolyte solution be refreshed at intervals of between around 0 and about 60 minutes, optimally between about 5 and about 15 minutes, since the samples and the bridge electrolyte solution mix somewhat at the liquid junction 14.

In a preferred embodiment, the bridge electrolyte solution is a 0.1 M KCl solution which is initially saturated with AgCl. The bridge electrolyte solution may contain a surfactant such as polyoxyl hydrogenated castor oil 25 (e.g., Arlatone G®) at a concentration of between 0.01% and 1.0%. Other types of surfactants can also be used, such as, e.g., Brij 35 (70 µl/l of solution), to minimize bubble formation. In an embodiment, the bridge electrolyte solution is prepared at room temperature and then saturated with excess AgCl. The solution containing suspended AgCl particles is then packaged in a sealed flexible container with no head space. This technique assures that the solution will remain saturated for AgCl at any storage temperature.

Enzyme Sensors

The above-described calibration and measurements using ion-sensors 22 is also contemplated for enzyme sensors. Such enzyme sensors are useful for the analysis of solutes other than $Na^+$, $K^+$, $Cl^-$, $Ca^+$, gases other than $pO_2$, $pCO_2$, hematocrit and pH. For example, enzyme sensors are useful for analysis of glucose, or lactate, or other proteins in a body fluid sample such as blood.

Equivalents

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

We claim:

1. A reference electrode comprising:
   (a) a reference sensor;
   (b) a bridge electrolyte channel in fluid communication with said reference sensor; and
   (c) a connector channel connected to the bridge electrolyte channel, said connector channel comprising a sample inlet channel and a sample outflow channel through which a sample may flow, a bridge electrolyte well for retaining a volume of a bridge electrolyte solution, and a bridge electrolyte port which connects said bridge electrolyte well with said bridge electrolyte channel;
   wherein said bridge electrolyte well is dimensioned to provide a liquid junction between the sample and the bridge electrolyte solution, and wherein said liquid junction has a width that exceeds the diameter of said bridge electrolyte port.

2. The reference electrode of claim 1, wherein the liquid junction comprises a surface area in the range of about 0.5 mm$^2$ to about 10 mm$_2$.

3. The reference electrode of claim 1, wherein said reference sensor comprises:
   (d) a support substrate;
   (e) a silver layer (Ag) deposited on said support substrate;
   (f) a silver chloride (AgCl) layer deposited on said Ag layer;
   (g) a glaze layer deposited on at least part of said AgCl layer; and
   (e) a gasket disposed on said glaze layer.

4. The reference electrode of claim 1, wherein said connector channel comprises a polymeric or metallic material that does not react with, or dissolve in, said bridge electrolyte solution.

5. The reference electrode of claim 4, wherein said polymeric material is a molded or machinable plastic.

6. The reference electrode of claim 5, wherein said polymeric material comprises acrylic, plexiglass, polycarbonate, or polyvinyl chloride.

7. The reference electrode of claim 4, wherein said metallic material comprises stainless steel, aluminum or platinum.

8. The reference electrode of claim 1, wherein said bridge electrolyte well is a round bottom well.

9. The reference electrode of claim 1, wherein said bridge electrolyte well is a flat bottom well.

10. The reference electrode of claim 1, wherein said bridge electrolyte well is a cone-shaped well.

11. The reference electrode of claim 1, wherein at least one of said sample outflow channel and said sample inlet channel each form a tilt angle of about 90° to about 180° relative to the longitudinal axis of the bridge electrolyte channel.

12. The reference electrode of claim 1, wherein said connector channel is located at a distance range from the reference sensor of between about 2 mm to about 10 mm, between about 2 mm to about 15 mm, or between about 2 mm to about 30 mm.

13. The reference electrode of claim 1, wherein said sample inlet channel is about 1 mm in diameter.

14. The reference electrode of claim 13, wherein said bridge electrolyte channel is about 0.5 mm in diameter.

15. The reference electrode of claim 13, wherein said sample outflow channel is about 2 mm in diameter.

16. The reference electrode of claim 1, wherein said bridge electrolyte channel is about 0.5 mm in diameter.

17. The reference electrode of claim 16, wherein said sample outflow channel is about 2 mm in diameter.

18. The reference electrode of claim 1, wherein said sample outflow channel is about 2 mm in diameter.

19. The reference electrode of claim 1, wherein said sample outflow channel and said sample inlet channel comprise a flexible tube that is about 1 mm to about 20 mm in diameter.

20. The reference electrode of claim 1, wherein said bridge electrolyte solution comprises KCl saturated with AgCl, with a chloride ion solution of about 0.1 M to about 0.5 M at the temperature said solution is stored and used.

21. A method for using a liquid junction reference electrode, comprising the steps of:
   (a) providing a reference electrode comprising a reference sensor; a bridge electrolyte channel in fluid communication with said reference sensor; and a connector channel connected to the bridge electrolyte channel, said connector channel comprising a sample inlet channel and a sample outflow channel through which a sample may flow, a bridge electrolyte well for retaining a volume of a bridge electrolyte solution, and a bridge electrolyte port which connects said bridge electrolyte well with said bridge electrolyte channel; wherein said bridge electrolyte well is dimensioned to provide a liquid junction between the sample and the bridge electrolyte solution, and wherein said liquid junction has a width that exceeds the diameter of said bridge electrolyte port;
   (b) providing a sample to said sample inlet channel;
   (c) providing a bridge electrolyte solution to said bridge electrolyte channel;
   (d) providing a force to said sample so that it flows toward said bridge electrolyte port;
   (e) providing a force to said bridge electrolyte solution so that it flows toward said bridge electrolyte port;
   (f) forming a liquid junction between said sample and said bridge electrolyte solution at said bridge electrolyte well with a surface area in the range of about 1 mm$^2$ to about 10 mm$^2$; and
   (g) taking a measurement.

22. A reference electrode comprising:
   (a) a reference sensor comprising:
      (i) a support substrate;
      (ii) a silver layer (Ag) deposited on said support substrate;
      (iii) a silver chloride (AgCl) layer deposited on said Ag layer;
      (iv) a glaze layer deposited on at least part of said AgCl layer; and
      (v) a gasket disposed on said glaze layer;
   (b) a bridge electrolyte channel in fluid communication with said reference sensor; and (c) a connector channel connected to the bridge electrolyte channel via a bridge electrolyte port, said connector channel comprising a sample inlet channel and a sample outflow channel through which a sample may flow, and a bridge electrolyte well for retaining a volume of a bridge electrolyte solution;

wherein said bridge electrolyte well is dimensioned to provide a liquid junction between the sample and the bridge electrolyte solution.

23. The reference electrode of claim 22, wherein said support substrate comprises a polymeric material or a ceramic material.

24. The reference electrode of claim 23, wherein said polymeric material comprises polyvinyl chloride (PVC), polyethylene, polycarbonate, polyacrylate, or polyimide.

25. The reference electrode of claim 23, wherein said ceramic material comprises aluminum oxide or silicium dioxide.

26. The reference electrode of claim 22, wherein one or more of said layers are screen printed layers or vapor deposited layers.

27. The reference electrode of claim 22, wherein said Ag layer is about 1 $\mu$m to about 15 $\mu$m thick.

28. The reference electrode of claim 22, wherein said Ag layer is at least about 1 $\mu$m thick.

29. The reference electrode of claim 22, wherein said AgCl layer is deposited on said Ag by electrodeposition on said Ag with a chloride electrolyte solution of between about 0.01 M and 1.0 M at a current density of between about 0.005 and about 0.5 mA/mm2 for about 30 seconds to about 20 minutes.

30. The reference electrode of claim 29, wherein said chloride electrolyte solution comprises NaCl, KCl, or CaCl.

31. The reference electrode of claim 30, wherein said chloride electrolyte solution has a pH range of about pH 1 to about pH 7, about pH 1 to about pH 5, or about pH 1 to pH 2.

32. The reference electrode of claim 22, wherein said glaze layer comprises alumina or silica.

33. The reference electrode of claim 32, wherein said glaze layer is at least about 10 $\mu$m thick.

34. The reference electrode of claim 33, wherein said glaze layer has a thickness of between about 10 $\mu$m and about 500 $\mu$m.

35. The reference electrode of claim 34, wherein said gasket is at least about 50 $\mu$m thick.

36. The reference electrode of claim 22, wherein said gasket layer comprises polyurethane, silicone rubber, polyvinyl chloride, fluoroelastomer, natural rubbers or synthetic rubber.

* * * * *